United States Patent [19]

Radisch, Jr. et al.

[11] Patent Number: 5,101,682

[45] Date of Patent: Apr. 7, 1992

[54] REINFORCED TUBING

[75] Inventors: Herbert R. Radisch, Jr., San Diego; Andrew F. Farr, Spring Valley, both of Calif.

[73] Assignee: InterVentional Technologies, Inc., San Diego, Calif.

[21] Appl. No.: 549,186

[22] Filed: Jul. 6, 1990

[51] Int. Cl.⁵ .............................................. F16C 1/20
[52] U.S. Cl. ................................... 74/502.6; 74/502.5; 428/632; 428/677; 138/143
[58] Field of Search .......................... 74/502.5, 502.6; 464/57, 60, 173, 174; 138/140, 143, 144; 428/632

[56] References Cited

U.S. PATENT DOCUMENTS

| | | | |
|---|---|---|---|
| 492,266 | 2/1893 | Browne | 464/183 |
| 732,415 | 6/1903 | Janet | 74/502.5 X |
| 779,374 | 1/1905 | Phillips | 464/60 |
| 2,748,805 | 6/1956 | Winstead | 138/76 |
| 2,960,712 | 11/1960 | Hayer | 15/179 |
| 3,015,969 | 1/1962 | Bratz | 74/502.5 |
| 3,063,303 | 11/1962 | Cadwallader | 464/174 X |
| 3,180,625 | 4/1965 | Wyzenbeek | 159/1 |
| 3,192,795 | 7/1965 | Pierce | 464/174 X |
| 3,240,082 | 3/1966 | Bratz | 464/174 |
| 3,261,225 | 7/1966 | Crouse | 74/501 |
| 3,628,352 | 12/1971 | Stuemky | 64/15 |
| 3,764,779 | 10/1973 | Kadoya et al. | 74/502.5 |
| 3,769,813 | 11/1973 | Okada | 64/2 R |
| 3,837,819 | 9/1974 | Hibbs, Jr. | 428/658 |
| 4,099,425 | 7/1978 | Moore | 74/502.5 |
| 4,103,075 | 7/1978 | Adam | 428/672 |
| 4,446,198 | 5/1984 | Shemenski et al. | 428/677 |
| 4,541,303 | 8/1985 | Kuzunishi | 74/502.5 |
| 4,620,569 | 11/1986 | von Glanstatten et al. | 138/132 |
| 4,634,805 | 1/1987 | Orban | 428/394 |
| 4,657,049 | 4/1987 | Fourty et al. | 138/133 |
| 4,823,847 | 4/1989 | Grosse et al. | 138/143 |
| 4,853,295 | 8/1989 | Shindo et al. | 428/632 X |
| 4,863,416 | 9/1989 | Gupta | 464/181 |

*Primary Examiner*—Leslie A. Braun
*Assistant Examiner*—Winnie Yip
*Attorney, Agent, or Firm*—Nydegger & Associates

[57] ABSTRACT

A reinforced tubing has an inner continuous hollow metallic tube. To strengthen the tube, a metallic helical structural member is bonded in tension by nickel or cobalt electroplating to the outside wall of the tube. Thus, a surrounding layer of electroplated material (i.e. nickel or cobalt) covers the tube and the structural member to bond the structural member to the tube. The individual coils of the helical structural member are spaced apart, so that the edges of successive coils do not touch or overlap. Importantly, the angular pitch between successive coils is in the range 20°-60°, the pitch being variable throughout the length of the tubing.

For applications wherein the tubing is to be used as a rigid platform, a longitudinal stiffening member may be bonded to the inside of the tube. Additionally, regardless of the particular application of the tubing, a polymeric coating may be molded onto the outside of the tube, the helical structural member, and the surrounding electroplated layer to cover and protect the tubing.

21 Claims, 1 Drawing Sheet

REINFORCED TUBING

FIELD OF THE INVENTION

The present invention pertains to a composite tubing for use in a wide variety of applications. More particularly, the present invention pertains to a reinforced tubing which can transmit rotational and translational motion. The present invention is particularly, though not exclusively, useful as a control cable or as a rigid platform.

BACKGROUND OF THE INVENTION

A large number of reinforced tubing devices have been introduced for use in a wide variety of applications. For example, flexible reinforced tubing is commonly used to transmit translational motion (i.e., push-pull) or rotational motion (i.e., torque) from a control apparatus to an object which is to be manipulated or moved. An example of one such device is the flexible shaft disclosed in U.S. Pat. No. 492,266, which can be used in dental applications and includes three coils soldered together under tension for translating torque to a small drill. As another example U.S. Pat. No. 3,261,225 discloses a control device, familiarly referred to as a "Bowden controller", that has an inner cable which slides within an outer helical supporting sheath for controlling the throttle of a motor. Yet another example of a reinforced tubing device is disclosed in U.S. Pat. No. 3,769,813 for a resilient torque tube that is reinforced with alternate layers of wire net and rubber and is useful in vehicle transmissions. With this in mind, one consideration in the design of reinforced tubing devices is the need for adequate tubing resilience (i.e., resistance to permanent deformation, kinking, and buckling under stress). In each of the above examples, the device or apparatus which is disclosed is designed to perform a certain specific function. It is sometimes desirable, however, that a single reinforced tubing device be adaptable for use in a wide variety of applications. Further, it may be desirable that the reinforced tubing be highly flexible for certain applications, such as for providing a conduit for fluid flow. It may also be desirable that the tubing retain sufficient strength to function effectively as a torque transmitter.

While each of the reinforced tubing devices discussed above can fulfill at least one of the above requirements, there is still a need for a single reinforced tubing device which can be used interchangeably in a variety of applications which will simultaneously rely on several of the characteristics mentioned above. To satisfy this need, the present invention recognizes that a single reinforced tubing device can be provided which is relatively strong, flexible, and which does not easily kink, permanently deform, or buckle under stress.

Accordingly, it is an object of the present invention to provide a reinforced tubing device which is relatively flexible and relatively strong. It is a further object of the present invention to provide a reinforced tubing device that efficiently transmits translational and rotational motion without easily buckling, kinking, or permanently deforming. Another object of the present invention is to provide a reinforced tubing device which can be used in a wide variety of applications. Yet another object of the present invention is to provide a reinforced tubing device that is easy to use and relatively cost effective to manufacture.

SUMMARY

A reinforced hollow tube has a continuous annular wall that defines an inner lumen and at least one helical structural member which is bonded in tension to the outer surface of the tube wall. The helical structural member may be a wire or ribbon, and may include a single strand or a plurality of strands. Importantly, the helical structural member is made of a material which, when bonded in tension to the tube wall, provides hoop stress to strengthen the tube wall. Additionally, the material of the helical stuctural member should be compatible with the material of the tube wall to provide for tight, permanent bonding of the helical member to the tube wall. To these ends, the helical structural member preferably is made of molybdenum, tungsten, cobalt, steel, nickel, or combinations thereof, while the tube is preferably made of steel, gold, platinum, or combinations thereof. For the preferred embodiment, the helical structural member is bonded to the tube wall by nickel electroplating or by cobalt electroplating. Accordingly, a thin layer of the electroplating material covers both the helical structural member and the tube.

The helical structural member (or members) forms a series of coils which are spaced apart (i.e., successive coils do not contact each other at their respective edges). An angular pitch between successive coils is established to provide for both steerability (i.e., bending) of the tubing and torque transmission through the tubing. Pitch angles of between ten (10) and sixty (60) degrees have been found to be effective for this purpose. This pitch may be variable, if desired, throughout the length of the tubing as steerability and torque transmission requirements dictate. For example, a relatively low (about twenty (20) degrees) pitch may be used to provide for greater flexibility (and, hence, steerability). On the other hand, a relatively high pitch (forty-five (45) degrees or greater) will provide for better torque transmission. Alternatively, the pitch may be established to be approximately thirty (30) degrees to provide for intermediate degrees of both torque transmission and steerablity. Importantly, the pitch structural member which is sufficiently large to reduce the likelihood that the electroplating layer will crack when the tube is bent.

In addition to the structure disclosed above, a stiffening member may be longitudinally disposed within the tube and bonded to the inner wall of the tube, to impart rigidity to the tube. Also, the entire combination of tube, stiffening member, and helical structural member may be encased in a polymeric coating which can be molded, extruded, or otherwise deposited around the tubing.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
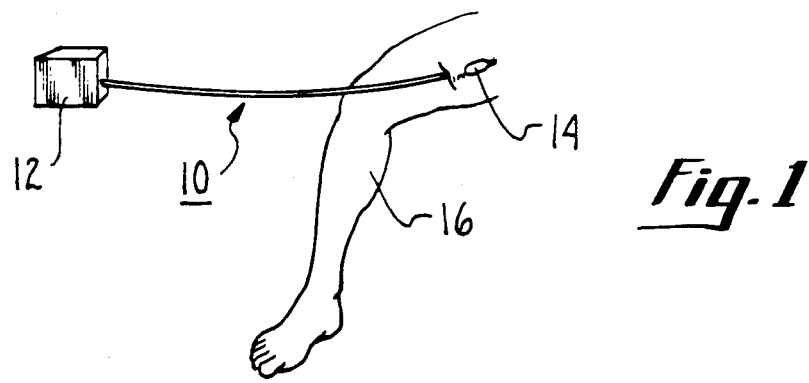
FIG. 1 is a perspective view of the novel reinforced tubing in one intended environment, showing the tubing in operative association with a balloon catheter device.

Initially referring to FIG. 1, it can be seen that a reinforced tubing, generally designated 10, may be operatively associated with various ancillary devices in various diverse applications. For example, FIG. 1 shows tubing 10 operatively associated with an angioplasty surgery control apparatus 12 and an expandable angioplasty balloon 14. In the application of tubing 10 shown in FIG. 1, tubing 10 is a flexible control cable and guide wire for imparting translational motion to balloon 14 and for transmitting torque from apparatus 12 to balloon 14. Tubing 10 is also a conduit for communicating fluid to balloon 14 to inflate balloon 14 in connection with an angioplasty surgery procedure on a patient 16. While FIG. 1 illustrates one potential application of tubing 10, it is to be understood that the application shown in FIG. 1 is merely exemplary. As a further example of a potential application for tubing 10, tubing 10 could be used as a connector between a fluid source and a fluid receiver for fluid communication applications requiring a strong yet flexible hose connector, or as a control cable and fluid conduit in a surgical atherectomy apparatus.

Figure 2:
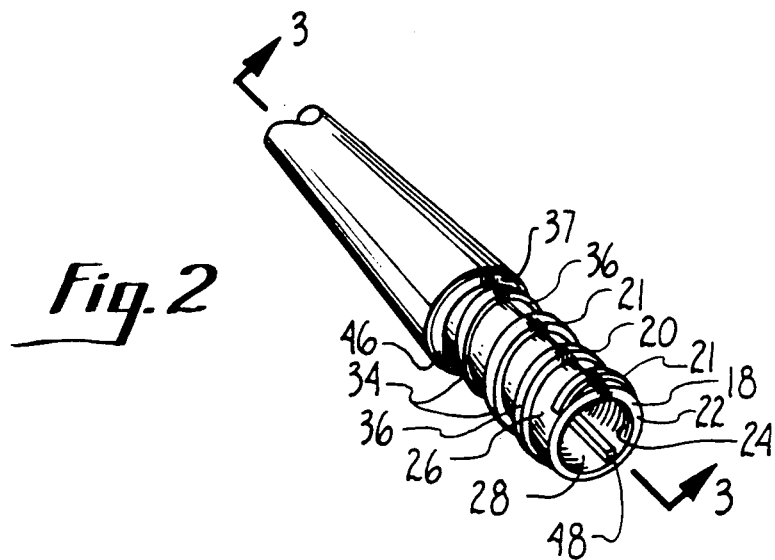
FIG. 2 is an isometric view of the novel reinforced tubing of the present invention with the polymeric coating and electroplating layer cut away for clarity.
Figure 3:
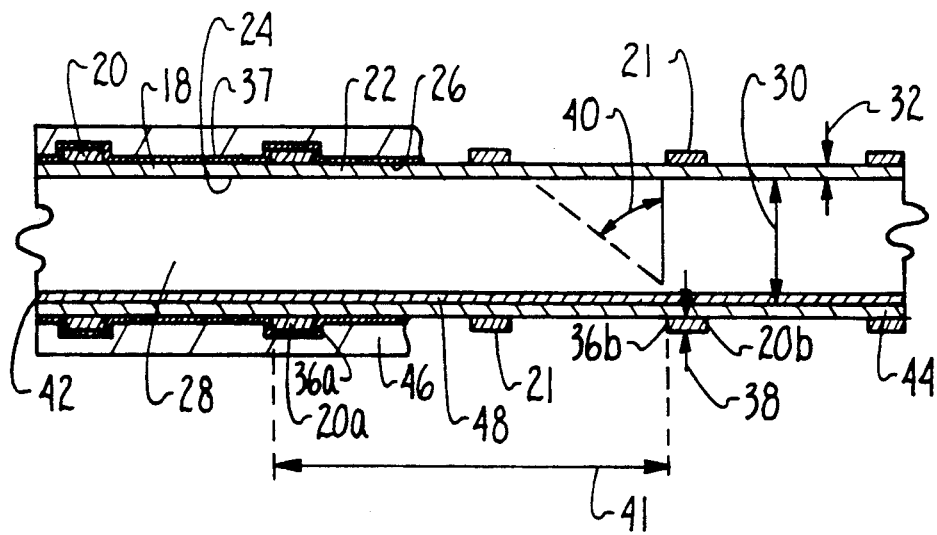
FIG. 3 is a cross-sectional view of the novel reinforced tubing as seen along the line 3—3 in FIG. 2.

Turning now to FIGS. 2 and 3, the details of reinforced tubing 10 can be seen. There, tubing 10 is shown to include a hollow inner tube 18 and a helical structural member 20. FIGS. 2 and 3 also show a helical structural member 21 which is attached to hollow inner tube 18 in juxtaposition with the helical structural member 20. As can be appreciated, additional structural members can be provided and attached to tube 18 in juxtaposition with structural members 20, 21. As best shown in FIG. 3, tube 18 has a continuous, substantially cylindrical annular wall 22 which defines an inner surface 24 and an outer surface 26. Wall 22 of tube 18 also defines a central hollow lumen or passageway 28, through which fluid or gas can flow in connection with, for example, angioplasty surgery applications of tubing 10. Importantly, the dimensions of tube 18 (and tubing 10) may be established as appropriate for the particular application of tubing 10. For example, when tubing 10 is being used as a guide wire/control cable for angioplasty surgery applications, inner diameter 30 of tube 18 may be approximately fourteen thousandths (0.014) of an inch, while the thickness 32 of wall 22 may be one thousandth (0.001) of an inch thick. It is to be understood, however, that the thickness 32 of wall 22 and inside diameter 30 of tube 18 may be larger or smaller than the above exemplary dimensions, depending on the particular application of tubing 10. Further, the length of tubing 10 may be established as appropriate for the particular application of tubing 10. For example, tubing 10 may have a length which can vary between a few inches and several yards.

Additionally, tube 18 is preferably made of a strong yet flexible material, such as stainless steel, gold, platinum, or combinations thereof. As the skilled artisan will appreciate, the material of tube 18 may also be selected to be compatible certain applications of tubing 10 may dictate that the material of tube 18 be chemically compatible with certain fluids which may be communicated through passageway 28 of tube 18, and further that the material of tube 18 be non-toxic and non-oxidizing.

Still referring to FIGS. 2 and 3, the helical structural member 20 is shown bonded to outer surface 26 of tube wall 22. More particularly, as shown in FIG. 2, helical structural member 20 is bonded to tube 18 to form a succession of spaced apart coils 34 whose respective edges 36 do not contact each other. Also, although the present invention uses a wire for member 20, it is to be understood that the geometry of member 20 may be any geometry suitable for providing structural support for tube wall 22, such as a ribbon. Furthermore, as indicated above, a member 20 may be used individually or in combination with other members, e.g. member 21. Importantly, member 20, and all other members 21, should be made of a material which, when helically bonded in tension to the tube wall 22, provides sufficient hoop stress to structurally strengthen tube wall 22. In addition, as can be appreciated from the foregoing discussion, the material of member 20 must be compatible with the material of tube wall 22 to provide for effective electroplating. In the present invention, helical structural member 20 is composed of tungsten, but it is to be understood that other materials may discussed above, such as molybdenum, cobalt, stainless steel, nickel, or combinations thereof.

For the embodiment shown in FIGS. 2 and 3, member 20 is bonded to tube wall 22 by nickel electroplating, cobalt electroplating, or other well-known electroplating methods which are appropriate for the particular materials of tube wall 22 and member 20. FIGS. 2 and 3 show that a surrounding layer 37 of nickel or cobalt is electroplated over both helical structural member 20 and tube 18, to bond member 20 to tube 18.

In addition to the material requirements of helical structural member 20 disclosed above, it will be recognized by the skilled artisan that the dimensions and configuration of member 20 will have a significant effect on the operational capabilities of tubing 10. On the one hand, these variables must be selected to provide sufficient structural support for tube wall 22. On the other hand, (for certain applications of tubing 10) the variables must be selected to minimize the cross section of tubing 10. For example, when tubing 10 is to be used in the angioplasty surgery application shown in FIG. 1, thickness 38 of helical structural member 20 is approximately two thousandths (0.002) of an inch thick. For other applications which require even greater strength of tubing 10, helical structural member 20 may be relatively thicker.

As the skilled artisan will also readily appreciate, an angular pitch 40 between the successive coils 34 of helical structural member 20, can be selected to provide for both tubing 10 flexibility as well as for sufficient torque transmission characteristics of tubing 10. In fact, the present invention envisions a pitch 36 along the length of tubing 10 which can be varied between ten (10) and sixty (60) degrees, as flexibility and torque transmission requirements dictate. For example, pitch 40 may be relatively high (about forty-five (45) degrees) at end 42 of tubing 10 for maximum torque transmission. Pitch 40 may then be gradually or suddenly reduced to about thirty (30) degrees at the end 44 of tubing 10 to provide for more flexibility of tubing 10 near end 44.

As seen in reference to FIG. 3, the pitch 40 also establishes the distance 41 between adjacent coils of member 20. Stated differently, adjacent coils of member 20 are spaced apart a distance 41, and do not touch each other. More particularly, taking coils 20a and 20b as an example, edge 36a of coil 20a does not touch edge 36b of coil 20b. Importantly, pitch 40 (and, hence, distance 41) are established to be large enough to reduce the likelihood of cracking electroplating layer 37 when tubing 10 is bent. Consequently, the lower limit of pitch 40 (i.e., ten (10) degrees) is established in part by the requirement that pitch 40 (and distance 41) remain large enough to reduce the likelihood of cracking of layer 37.

It is to be appreciated that the structure disclosed above results in several advantages. First, tubing 10 is a strong, yet flexible hollow tube which can effectively transmit both translational motion and rotational motion (i.e., torque). Thus, tubing 10 can be used as a control cable or torque conveyor in a variety of applications. Second, the structure disclosed above results in a tubing 10 which will not readily kink or permanently deform when bent. Third, tubing 10 will not readily buckle under tensile or compressive stress, such as what may be generated when torque is being transmitted through tubing 10.

FIGS. 2 and 3 also show that tube 18, helical structural member 20, and electroplating layer 37 can be encased in a polymeric coating 46. As shown, coating 46 surrounds and covers tube 18, helical structural member 20, and layer 37. Coating 46 may be deposited over tube 18, member 20, and layer 37 by any suitable means, such as by molding or extruding coating 46 onto tube 18, member 20, and layer 37. As was the case for the materials of tube 18 and member 20, certain applications of tubing 10 may require that the material of coating 46 be chemically inert for compatibility with various fluids or chemicals. Polyetherimid and polyethylene have been found to be suitable materials for polymeric coating 46.

As disclosed above, certain applications of tubing 10 may require a tubing 10 which is substantially rigid. To this end, a stiffening member, such as the elongated stiffening bar 48 shown in FIGS. 2 and 3, may be bonded to wall 22 of tube 18. Accordingly, stiffening bar 48 is preferably made of a rigid material which is compatible with the material of tube 18, to facilitate bonding bar 48 to wall 22 of tube 18. While FIGS. 2 and 3 show a bar 48 that is essentially an elongated parallelepiped, any suitable geometry may be used for bar 48. For example, bar 48 may be an elongated solid cylinder. Also, for applications which require a smooth inner surface 24, the bar 48 may be embedded in coating 46 or otherwise attached to tubing 10 to provide the required stiffness.

In the method of manufacturing tubing 10, reference is made to FIGS. 2 and 3. Tube 18 is initially formed in the configuration described above. Then, structural member 20 is wrapped or wound in tension around tube 18 in the helical configuration shown in FIGS. 2 and 3. The assembly which consists of tube 18 and member 20 is next immersed in an electroplating bath (not shown) which contains the material of layer 37 in liquid solution. An appropriate voltage is applied to an anode which is also immersed in the electroplating bath. In accordance with well-known principles, the material of layer 37 is deposited during the electroplating process onto both tube 18 and member 20, which collectively function as the cathode of the electroplating solution. Consequently, after layer 37 is deposited, layer 37 bonds member 20 to tube 18.

Subsequent to the electroplating process described above, tube 18, member 20, and layer 37 are encased in polymeric coating 46 by any well-known means. For example, polymeric coating 46 can be molded, extruded, or otherwise deposited onto tube 18, member 20, and layer 37.

It is to be understood that the details of the operation of tubing 10 will vary according to the particular application of tubing 10. When tubing 10 is to be used as a torque transmitter/control cable, for example, stiffening bar 48 is dispensed with and end 42 of tubing 10 is operatively associated with the particular control apparatus being used, such as the apparatus 10 shown in FIG. 1, or a motor throttle (not shown) or even a person's hand (not shown). End 44 of tubing 10, in contrast, is attached to the mechanism being manipulated, such as the angioplasty balloon 14 shown in FIG. 1. Translational motion and torque may then be transmitted through tubing 10 from the particular control apparatus being used to the mechanism being manipulated. At the same time, because inner tube 18 is hollow, fluid or gas may be communicated between ends 42 and 44 of tubing 10.

While the particular reinforced tubing as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A flexible torque transmission cable which comprises:
   a hollow tube having a continuous wall defining an inner surface and an outer surface;
   a helical structural member positioned in tension around said outer surface of said wall for strengthening said tube; and
   an electroplatable metal surrounding layer electroplated over said structural member to continuously coat said tube and said structural member and bond said structural member to said tube.

2. A torque transmission cable as recited in claim 1 wherein said helical stuctural member is a metallic ribbon.

3. A torque transmission cable as recited in claim 1 wherein said helical structural member is a metallic wire.

4. A torque transmission cable as recited in claim 2 wherein said metallic ribbon comprises a plurality of strands.

5. A torque transmission cable as recited in claim 3 wherein said metallic wire comprises a plurality of strands.

6. A torque transmission cable as recited in claim 1 wherein said helical structural member comprises a material selected from a group consisting of tungsten, cobalt, stainless steel, molybdenum, nickel, and combinations thereof.

7. A torque transmission cable as recited in claim 6 wherein said tube comprises a material selected from a group consisting of stainless steel, gold platinum, and combinations thereof.

8. A torque transmission cable as recited in claim 7 wherein said surrounding layer is nickel.

9. A torque transmission cable as recited in claim 7 wherein said surrounding layer is cobalt.

10. A torque transmission cable as recited in claim 1 wherein said helical structural member defines a plurality of coils, said helical structural member defines a plurality of coils, said helical structural member being formed with a pitch between successive said coils in a range from ten (10) to sixty (60) degrees.

11. A torque transmission cable as recited in claim 10 wherein said pitch is variable throughout said torque transmission cable.

12. A torque transmission cable as recited in claim 1 further comprising a continuous layer of polymeric material surroundingly molded over said tube, said helical structural member, and said surrounding layer.

13. A torque transmission cable which comprises:
   a hollow tube having a continuous wall defining an inner surface and an outer surface;
   a stiffening member disposed longitudinally within said tube, said stiffening member being bonded to said inner surface of said tube wall;
   a helical structural member positioned in tension around said outer surface of said wall for strengthening said tube; and
   an electroplatable metal surrounding layer electroplated over said tube and said structural member to continuously coat said tube and said structural member and bond said structural member to said tube.

14. A flexible reinforced tubing apparatus, which comprises;
   at least one continuous metallic helical structural member defining an axial bore therethrough;
   a metallic hollow tube axially disposed within said bore of said helical structural member, said tube having a continuous wall, said helical structural member being positioned in tensile stress against said wall; and
   an electroplatable metal surrounding layer electroplated over said tube and said structural member to continuously coat said tube and said structural member and bond said structural member to said tube.

15. A reinforced tubing apparatus as recited in claim 14 wherein said helical structural member is a ribbon.

16. A reinforced tubing apparatus as recited in claim 14 wherein said helical structural member comprises a material selected from a group consisting of tungsten, cobalt, stainless steel, molybdenum, nickel, and combinations thereof.

17. A reinforced tubing apparatus as recited in claim 16 wherein said tube comprises a material selected from a group consisting of stainless steel, gold, platinum, and combinations thereof.

18. A reinforced tubing apparatus as recited in claim 17 wherein said surrounding layer comprises an element selected from a group consisting of nickel and cobalt.

19. A reinforced tubing apparatus as recited in claim 14 wherein said helical structural member defines a plurality of coils, each of said coils being distanced from its adjacent coils, said helical structural member being formed with a pitch between successive coils in a range from ten (10) to sixty (60) degrees, said pitch being variable throughout said reinforced tubing apparatus.

20. A reinforced tubing apparatus as recited in claim 14 further comprising a continuous layer of polymeric material surroundingly molded over said helical structural member, said tube, and said layer.

21. A reinforced tubing apparatus which comprises:
   at least one continuous metallic helical structural member defining an axial bore therethrough;
   a metallic hollow tube axially disposed within said bore of said helical structural member, said tube having a continuous wall, said helical structural member being positioned in tensile stress against said wall;
   a stiffening member disposed longitudinally within said tube, said stiffening member being bonded to said tube wall; and
   an electroplatable metal surrounding layer electroplated over said tube and said structural member to continuously coat said tube and said structural member and bond said structural member to said tube.

* * * * *